United States Patent [19]
Bonnell et al.

[11] Patent Number: 5,540,649
[45] Date of Patent: Jul. 30, 1996

[54] POSITIONER FOR MEDICAL INSTRUMENTS

[75] Inventors: Leonard Bonnell, Huntingdon Valley, Pa.; John G. Aceti, Cranbury, N.J.

[73] Assignee: Leonard Medical, Inc., Huntingdon Valley, Pa.

[21] Appl. No.: 134,206

[22] Filed: Oct. 8, 1993

[51] Int. Cl.⁶ .............. A61B 1/01; B65H 51/18
[52] U.S. Cl. .......... 600/114; 600/102; 600/126; 414/431; 414/746.7; 294/106
[58] Field of Search ............... 128/4–7, 772, 128/776, 11; 604/156, 164, 30; 606/130; 73/866.5; 414/431, 746.7; 226/186, 187, 89, 90, 190; 198/746, 747, 861.1, 861.5; 254/30, 333, 264, 396; 294/106; 227/30, 124

[56] References Cited

U.S. PATENT DOCUMENTS

| | | | |
|---|---|---|---|
| 1,537,545 | 5/1925 | Morton | 254/396 |
| 2,948,513 | 8/1960 | Krohn-Holm | 254/396 |
| 3,871,618 | 3/1975 | Funk | 254/30 |
| 4,054,128 | 10/1977 | Seufert et al. | 128/4 |
| 4,184,510 | 1/1980 | Murry et al. | 604/30 X |
| 4,517,963 | 5/1985 | Michel | 128/6 |
| 4,566,358 | 1/1986 | Ducanis | 414/431 |
| 4,856,354 | 8/1989 | Overbay | 73/866.5 |
| 5,018,509 | 5/1991 | Suzuki et al. | 128/6 |
| 5,104,103 | 4/1992 | Auchinleck et al. | |
| 5,154,723 | 10/1992 | Kubota et al. | 128/4 X |
| 5,184,603 | 2/1993 | Stone | 128/11 |
| 5,243,967 | 9/1993 | Hibino | 128/6 |
| 5,282,472 | 2/1994 | Companion et al. | 128/7 X |
| 5,318,442 | 6/1994 | Jeffcoat et al. | 128/776 X |
| 5,318,541 | 6/1994 | Viera et al. | 604/164 X |

FOREIGN PATENT DOCUMENTS

| | | | |
|---|---|---|---|
| 483721 | 8/1917 | France | 414/431 |
| 3710296 | 10/1988 | Germany | 294/106 |

OTHER PUBLICATIONS

Endex brochure, Endex Endoscopy Positioning System, Advancing the scope of endoscopy, Apr. 1993.
AESOP brochure, "Get an Extra Hand with Your Procedures with Robotics", 1993.

*Primary Examiner*—Richard J. Apley
*Assistant Examiner*—John P. Leubecker
*Attorney, Agent, or Firm*—Fish & Richardson P.C.

[57] ABSTRACT

The invention features a remote-controlled device for selectively positioning a medical instrument within a predetermined region of space. The remote-controlled device has a motor which provides mechanical energy to the remote-controlled device, a driver that is coupled to the motor and that has a predetermined relationship with the motor. The driver physically engages the medical instrument and converts the mechanical energy into controlled motion of the medical instrument. The remote-controlled device receives control signals from a remote location that direct the motor to supply a predetermined amount of mechanical energy, whereby the driver, with the predetermined relationship with the motor, selectively positions the medical instrument within the region of space.

15 Claims, 3 Drawing Sheets

POSITIONER FOR MEDICAL INSTRUMENTS

BACKGROUND

This invention relates to devices for positioning medical instruments.

Surgical procedures, e.g., those involving minimally invasive endoscopic surgery, require simultaneous use of numerous instruments by a physician. Often the procedure is complicated and one or more assistants may be required to hold one or more of these instruments in position. These assistants tend to congest the area around the operating table and restrict movement by the physician performing the surgery.

To address this problem, arms to hold surgical equipments have been suggested. For example, Bonnell (1989, U.S. Pat. No. 4,863,133, by one of the inventors here) discusses an articulated instrument support arm that employs vacuum switch controls to set the position of the arm with lightly loaded restraint. Milo (1975, U.S. Pat. No. 3,858,578) describes a flexible arm for holding surgical instruments, the joints of which can be simultaneously locked in place, using hydraulic pressure to tension a cable extending axially through the assembled arm elements. Poletti (1972, U.S. Pat. No. 3,638,973) and Kimoshita (1976, U.S. Pat. No. 3,986,692) describe jointed arms which can be fixed in position by hydraulic pressure.

SUMMARY

In general, in one aspect, the invention features a remote-controlled device for selectively positioning a medical instrument within a predetermined region of space. The remote-controlled device has a motor which provides mechanical energy to the remote-controlled device, a driver that is coupled to the motor and that has a predetermined relationship with the motor. The driver physically engages the medical instrument and converts the mechanical energy into controlled motion of the medical instrument. The remote-controlled device receives control signals from a remote location that direct the motor to supply a predetermined amount of mechanical energy, whereby the driver, with the predetermined relationship with the motor, selectively positions the medical instrument within the region of space.

At various times during surgery, a surgeon will require that a surgical instrument be repositioned. The invention permits the surgeon to act as an orchestra leader, directing his or her surgical team through a procedure, by providing a surgeon with the ability to precisely position an instrument, e.g., a powered surgical instrument or an endoscopic camera, for a surgical procedure from a remote location, allowing the surgeon to leave the vicinity of the instrument and to position himself or herself at various desired locations around the patient. The invention further permits the surgeon to precisely position the instrument by means of a foot control or some other controlling mechanism that frees the surgeon from having to position the instrument manually. The surgeon is permitted to use the freed hand for some other purposes, e.g., to better employ tactile control or monitoring of the patient, e.g., in positioning or manipulating the limbs.

Embodiments of the invention may include one or more of the following features. The device is remote-actuated by a foot-controlled switch. The device is remote-controlled by an electromagnetic-wave (e.g., infrared or RF radiation) transmitter. The device is steam-autoclavable. The controlled motion of the device is in a longitudinal direction. The driver includes at least one drive wheel having a V-shaped groove disposed in the surface of the wheel in a plane perpendicular to the axis of rotation of the wheel for engaging the medical instrument. The device includes at least one support wheel for providing a pre-load to an outer surface of the medical instrument. The medical instrument is an endoscope.

The invention permits the surgeon to be his or her own camera operator, when employed with an endoscopic camera (e.g., a laparoscope). This is very important since usually only the surgeon knows exactly what she is looking at, and time-consuming communication between the surgeon and a camera operator may be avoided, thereby reducing the overall time required to complete a surgical procedure. The invention is easy to operate and allows remote-controlled adjustment of the camera position to achieve e.g., optimal framing (e.g., centering on the most important part of the surgical field and adjusting the relative degree of closeness to the surgical field) of the picture, while remaining far less obtrusive to the operating surgeon than having another person operating the camera, who would likely impede access to the surgical site.

Because the invention is steam-autoclavable, the invention may be used in a surgical environment without requiring the use of space-consuming and view-obstructing protective plastic bags, or the like.

In general, in another aspect, the invention includes the features of a remote-controlled device for selectively positioning a medical instrument within a predetermined region of space which includes an instrument-supporting, articulated support arm. The arm has a distal end capable of supporting an instrument in the region of a surgical operating site and has at least one joint that supports a movable distal support element relative to a proximal support. The joint is associated with a mode selector. The remote-controlled device is coupled to the distal support element of the support arm.

When used in conjunction with a support arm, the invention permits the surgeon to leave the surgical area, e.g., to consult with other surgeons who may not be prepared to enter the surgical area, while being able to maneuver e.g.., an endoscopic camera to achieve different views of the patient, if desired.

Embodiments of the invention may also include the following features. The support arm has structure capable, upon selection of a first mode of operation by the selector, of enabling relatively free motion of the joint for achieving a desired position of the medical instrument. The joint has structure capable, upon selection of a second mode of operation by the selector, to set the position of the instrument in space with lightly loaded restraint.

DESCRIPTION

Figure 1:
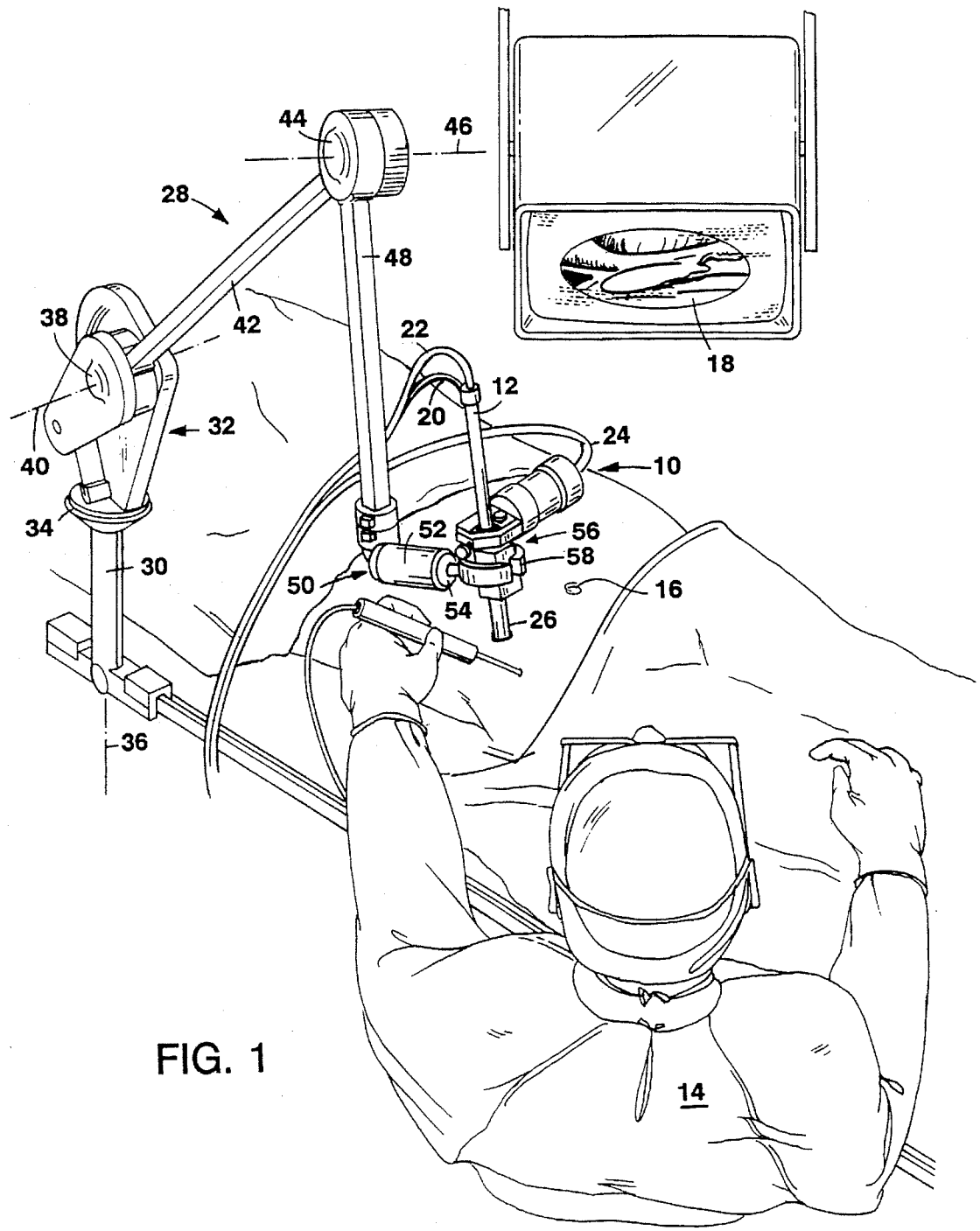
FIG. 1 is a somewhat diagrammatic perspective view of a surgeon employing the instrument-positioning device of the invention for positioning an instrument during surgery, e.g., on a patient's abdomen.

Referring to FIG. 1, an instrument-positioning device 10 of the invention is coupled to an endoscopic camera 12 (e.g., a laparoscope which has a shaft with a length of about 35 cm and outer diameter of about 10 mm), and allows a surgeon 14 to remotely control the position of the laparoscope at a desired location about the surgical site, e.g., as shown in the figure, a patient's abdomen 16, or other space, to achieve a desired view from inside the body on a video monitor 18. The source of illumination for the camera is supplied by a fiberoptic cable 20, while the image signals from the camera are carried on a cable 22. Cable 24 delivers control signals from a foot-operated, wet-cell rechargeable battery, DC power source (FIG. 4) to the instrument-positioning device. The control signals direct the instrument-positioning device to selectively position the laparoscope in and out of a cannula 26 to achieve narrower and wider fields-of-view on monitor 18.

The instrument-positioning device 10 and the cannula 26 are held fixedly in a desired position by a support arm 28, e.g., a Leonard Arm™ available from Leonard Medical of Huntingdon Valley, Pa., U.S.A., described in U.S. Pat. No. 4,863,133, issued to Bonnell (a co-inventor here) on Sep. 5, 1989, the entire disclosure of which is hereby incorporated by reference herein. The support arm consists of a vertical support post 30, a shoulder assembly 32 constructed for rotation at 34 about axis 36 and including shoulder joint 38 constructed for rotation about axis 40; upper arm 42; elbow joint 44 constructed for rotation about axis 46; forearm 48; and wrist assembly 50, including a wrist joint 52, e.g., a pair of spherical joints adapted to swivel independently of each other. At the end of the wrist assembly there is provided a quick disconnect assembly 54 for receiving an instrument clamp 56.

Figure 2:
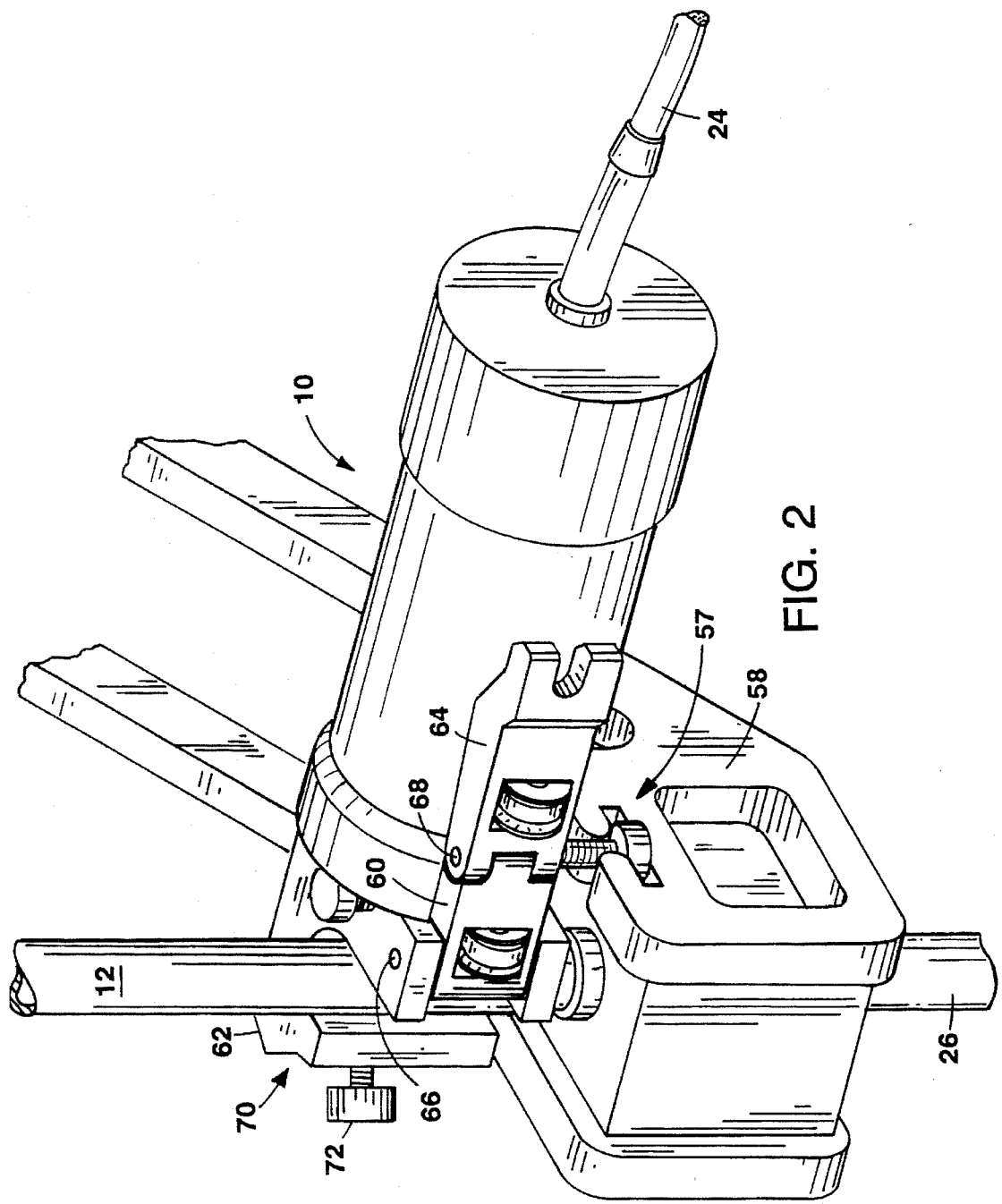
FIG. 2 is a perspective side view of an instrument-positioning device of the invention.

The cannula 26, extending through a puncture in the flesh to provide a conduit into a region of the body, e.g., the abdomen or knee, is gripped by the jaws 58 of clamp 56, while the instrument-positioning device is attached to the gripper by means of a boutonniere pin arrangement 57 (FIG. 2). Because the actuator is attached to the gripper at the end of the wrist assembly, the actuator is allowed to follow the motion of the laparoscope, accommodating any reasonable shift of the laparoscope without change in performance.

The instrument-positioning device is designed to attach onto a support arm after the laparoscope is in place, which allows the surgeon freedom to grossly position the laparoscope about the surgical site before attaching the actuator. The instrument-positioning device is roughly cylindrical and as small as practical, and, e.g., in the embodiment shown, the device has with a diameter of about ¾-inch to 1 inch and a length of about 5-7 inches. For example, during a Nissen fundoplication, it may be necessary for a surgeon to reposition the angle of the laparoscope relative to the patient, and a large attachment to the laparoscope would interfere with the patient's body and thereby limit the mobility range of the laparoscope (and thus the surgeon's viewing range inside the patient). In addition, a large attachment to the laparoscope would obscure the surgeon's view of the surgical site.

As shown in FIG. 2, the actuator attaches to the laparoscope using a three-bar linkage mechanism including a proximal link 60, a main bracket 62, and a distal link 64. Proximal link 60 is attached to main bracket 62 via a proximal pivot point 66 that allows the proximal link to pivot away from the laparoscope 12. Similarly, distal link 64 pivots about the proximal link at a distal pivot point 68. The distal link attaches to the distal end 70 of main bracket 62 by a retention element 72, e.g., a screw or lever.

The instrument-positioning device may be freely removed without disturbing the laparoscope by releasing the retention element to allow the distal link to pivot about the proximal link and simultaneously permitting the proximal link to rotate about the proximal pivot point.

Figure 3:
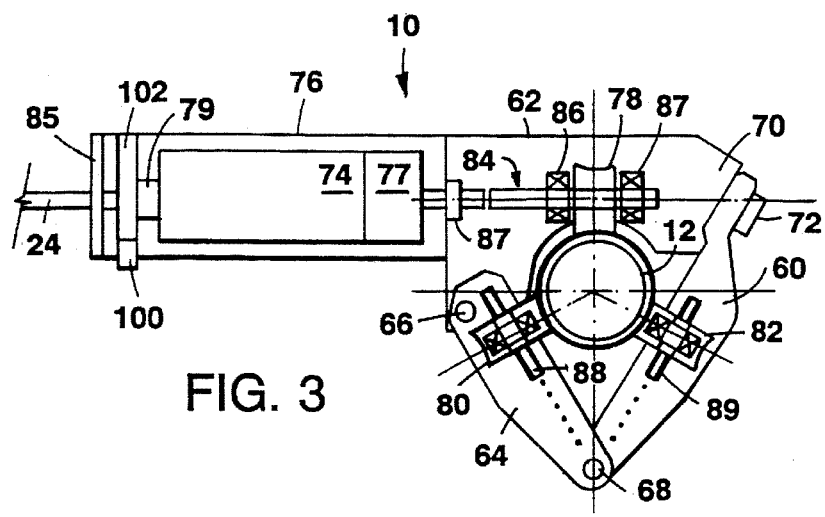
FIG. 3 is a schematic top view of an instrument-positioning device of the invention.

Referring to FIG. 3, instrument-positioning device 10 has a motor 74, a motor housing 76, a gear head 77 (e.g., a 200:1, or alternatively, a 100:1 gear head), a main bracket 62, proximal and distal links 60 and 64, respectively, a drive wheel 78, and proximal and distal support wheels 80, and 82, respectively.

The instrument-positioning device employs three stainless steel wheels, which press firmly against the shaft of the laparoscope, to selectively position the laparoscope. The wheels are equally spaced around the laparoscope shaft (i.e, the wheels are spaced 120° apart) to provide a balanced load, and frictionally drive the scope. That is, static friction transfers the rotational motion of the wheel into lateral motion of the scope. There is a direct and important relationship between the maximum driving force and the normal force of the wheel against the laparoscope. The greater the normal force, the greater the driving force. The practical limit is the compressional strength of the laparoscope itself.

Drive wheel 78 is coupled to motor 74 via a stainless steel coupler (drive shaft) 84. Stainless steel, high-temperature, sealed ball bearings 86 and 87 rigidly hold the drive wheel in place on the shaft. Proximal and distal support wheels are mounted on springs 88 and 89 for flexibly pressing the wheels against the outer wall of laparoscope 12 to provide a force (pre-load) of about 20 pounds against the laparoscope. (A greater force may damage the laparoscope, while a lesser force would not provide the necessary retention force to withstand the normal dynamic loads on the laparoscope, e.g., tension transmitted to the laparoscope from movement of the camera cable 22.)

The drive wheel and the two support wheels have each been machined with a "V" groove to provide two points of contact between the outside surface of the wheel and the laparoscope. Because the normal force is applied across two points for each wheel, rather than at one point, e.g., a flat roller wheel, the instrument-positioning device 10 may accommodate high load levels.

Motion of the laparoscope is achieved with a miniature DC electric motor 74 adapted to run in either direction, thus permitting forward and reverse motion of the laparoscope. The gear train (e.g., motor 74 and gear head 77) additionally provides resistance to slippage. Without the motor's internal friction, the drive wheel would not be "braked" and the laparoscope would be free to move in and out of the cannula. The force required to overdrive the gear train is sufficiently high to prevent unintentional movement of the scope. The force is also sufficiently low that if the laparoscope is forcibly withdrawn from the instrument-positioning device, the gears are driven without any damage to the actuator mechanism.

In a preferred embodiment, a dynamic brake 79 is added to provide further resistance to slippage of the laparoscope. For example, the brake 79 may include a conventional switch located within the motor housing 76. When activated, the switch creates a short circuit across the windings of DC motor 74, immediately stopping the rotation of the motor and thereby preventing the laparoscope from drifting.

The internal parts of the instrument-positioning device are sealed from the external environment by a static o-ring seal 85 and a high-temperature sealed bearing 87, which allows the device to be steam autoclaved, thereby permitting the device to be employed in a surgical site without requiring it to be sealed inside a plastic bag or other protective covering.

Figure 4:
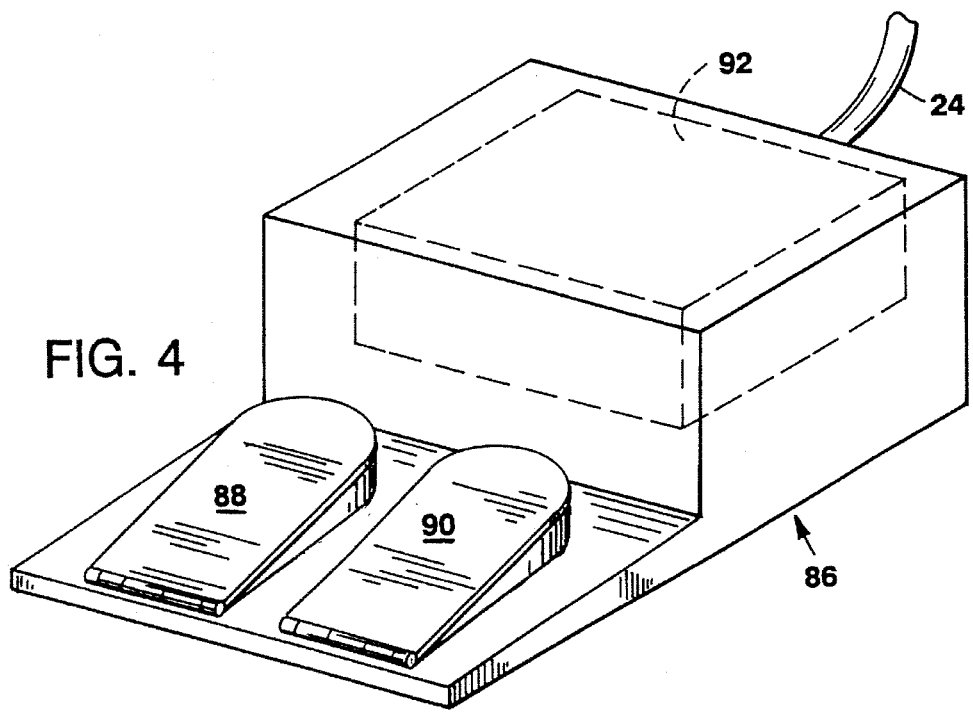
FIG. 4 is a schematic view of a remote actuator for use with the instrument-positioning device of the invention.
Figure 5:
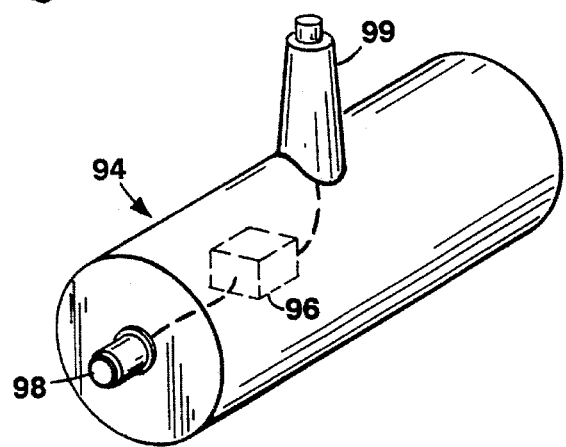
FIG. 5 is a somewhat perspective view of a remote actuator for use with the instrument-positioning device of the invention.

Referring to FIG. 4, the motor 74 is driven by one of many possible means in parallel. The primary remote actuator is a foot-activated controller 86. A pedal 88 acts as a switch to couple cable 22 in a forward polarity configuration to a wet-cell, rechargeable battery source 92, which when activated causes a forward polarity signal to be sent to the instrument-positioning device 10 that causes motor 74 to drive the laparoscope further into the cannula for a close-up view of the surgical area. A pedal 90 acts in a similar manner as pedal 88, except that pedal 90 couples cable 22 to the battery source in a reverse polarity configuration that causes motor 74 to drive the laparoscope out of the cannula.

The instrument-positioning device may also be controlled by an infrared control signal. The instrument-positioning device operates in forward or reverse direction depending on the frequency of the infrared signal. A remote transmitting device 94 is designed to be used by either the surgeon or an assistant, and may be attached, e.g., by means of a VEL-CRO® strap, to the shaft of a medical instrument to be used by the surgeon during a surgical procedure. Similar to a television remote control, the transmitter has a frequency generator 96 which drives a transmitter 98. The transmitter is cylindrical with a diameter of about ¾-inch and a length of about 1 inch. A thumb-activated control joy-stick 99 is disposed on the shaft of the transmitter to selectively generate forward or reverse control signals.

Built into the motor drive is an infrared diode receiver 100 (FIG. 3). This component receives the transmitted optical signal, converts it into electrical frequency which is fed to a decoder 102. The decoder determines the specific frequency and drives the appropriate motor relay. For either frequency, the motors is activated as long as the signal is present.

Other embodiments are within the scope of the claims.

A voice-activated remote actuator may also be employed to activate the motor to drive in forward and reverse directions.

An additional drive wheel may be disposed in the housing of the instrument-positioning device to selectively engage the laparoscope to rotate the laparoscope about its axis. This feature would provide a distinct advantage for use with a laparoscope in which the view port is not aligned with the longitudinal axis.

Additional configurations of the invention include providing for remote-controlled three-dimensional positioning of a medical instrument.

What is claimed is:

1. A device for selectively positioning an endoscope within the body of a patient during a medical procedure, said endoscope having an axially elongated shaft defining an axis, said device comprising a clamp having a first portion and a second portion pivotally attached to the first portion, said clamp being characterized by an open condition wherein the shaft of the endoscope can laterally pass between the first and second portions of said clamp, enabling the device to selectively engage with or disengage from the shaft of the endoscope, and by a closed condition wherein the shaft of the endoscope is laterally held between the first and second portions of said clamp, laterally coupling said device to the shaft of the endoscope, said first portion of said clamp comprising a main bracket and said second portion of said clamp comprising a proximal link having a proximal end pivotally attached to the main bracket and a distal end and a distal link having a proximal end pivotally attached to the distal end of said proximal link and a distal free end, said main bracket having a retention element for selectively locking said distal free end of said distal link thereto, a drive wheel rotatably coupled to said clamp and having a surface exposed for frictional engagement with the shaft of the endoscope, said drive wheel being rotatable about an axis that is perpendicular to the axis defined by the endoscope so that when the surface of said drive wheel engages with the shaft of the endoscope rotation of the drive wheel moves the endoscope in a direction along the axis defined by the endoscope, and a motor mechanically coupled to said drive wheel for rotating said drive wheel to cause controlled axial motion of endoscope within the body of the patient.

2. The device of claim 1 further comprising a second wheel coupled to said clamp and having a surface exposed for engagement with the shaft of said endoscope.

3. The device of claim 2 further comprising a spring coupled to said second wheel for urging the exposed surface of said second wheel against the shaft of the endoscope to provide a pre-load thereagainst.

4. The device of claim 1 further comprising a controller in communication with said motor for selectively operating said motor.

5. The device of claim 4 wherein said controller is a foot-controlled switch.

6. The device of claim 1 further comprising an electromagnetic-wave receiver coupled to said motor adapted to selectively operate said motor based on received electromagnetic-wave signals.

7. The device of claim 1 wherein said device has exposed outer surfaces that are formed from steam-autoclavable material.

8. The device of claim 1 wherein said drive wheel has a circumferential surface defining a V-shaped groove disposed in a plane perpendicular to the axis of rotation of said driver wheel, said V-shaped groove being sized and constructed to engage the shaft of the endoscope.

9. A device for selectively positioning an endoscope within the body of a patient during a medical procedure, said endoscope having an axially elongated shaft having an outer diameter and defining an axis, said device comprising a clamp having a first portion and a second portion pivotally attached to the first portion, said clamp being characterized by an open condition wherein the shaft of the endoscope can laterally pass between the first and second portions of said clamp, enabling the device to selectively engage with or disengage from the shaft of the endoscope, and by a closed condition wherein the shaft of the endoscope is laterally held between the first and second portions of said clamp, laterally coupling said device to the shaft of the endoscope, said first portion of said clamp comprising a main bracket and said second portion of said clamp comprising a proximal link having a proximal end pivotally attached to the main bracket and a distal end and a distal link having a proximal end pivotally attached to the distal end of said proximal link and a distal free end, said main bracket having a retention element for selectively locking said distal free end of said distal link thereto, a drive wheel rotatably coupled to said clamp and having a surface exposed for frictional engagement with the shaft of the endoscope, said drive wheel being rotatable about an axis that is perpendicular to the axis defined by the endoscope so that when the surface of said drive wheel engages with the shaft of the endoscope rotation of the drive wheel moves the endoscope in a direction along the axis defined by the endoscope, a motor mechanically coupled to said drive wheel for rotating said drive wheel to cause controlled motion of endoscope within the body of the patient in a direction along the axis defined by the endoscope, and a second wheel coupled to said clamp and having a surface exposed for frictional engagement with the shaft of the endoscope, said second wheel being rotatable about an axis that is perpendicular to the axis defined by the endoscope and that lies in a common plane with the axis of rotation of said drive wheel, the exposed surface of said second wheel being resiliently mounted with respect to said clamp so that the position of the exposed surface of said second wheel relative to the drive wheel yields in a direction perpendicular to both the axis defined by the endoscope and the axis of rotation of said second wheel in response to force applied by the endoscope to accommodate the outer diameter of the shaft of the endoscope and to apply a pre-load to the shaft with sufficient force to prevent slippage of the endoscope relative to said device.

10. The device of claim 9 further comprising a spring coupled to said second wheel for urging the exposed surface of said second wheel against the shaft of the endoscope to provide a pre-load thereagainst.

11. A system for selectively positioning an endoscope within the body of a patient during a medical procedure, said endoscope having an axially elongated shaft defining an axis, said system being of the type wherein the position of the endoscope relative to the patient is maintained by an instrument-supporting articulated support arm having a distal end capable of supporting the endoscope in the region of a surgical operating site, said system comprising a device for adjusting the axial position of the endoscope within the patient independent of the orientation of the support arm, said device being selectively attached to and detached from the distal end of said support arm, said device comprising a clamp having a first portion and a second portion pivotally attached to the first portion, said clamp being characterized by an open condition wherein the shaft of the endoscope can laterally pass between the first and second portions of said clamp, enabling the device to selectively engage with or disengage from the shaft of the endoscope, and by a closed condition wherein the shaft of the endoscope is laterally held between the first and second portions of said clamp, laterally coupling said device to the shaft of the endoscope, said first portion of said clamp comprising a main bracket and said second portion of said clamp comprising a proximal link having a proximal end pivotally attached to the main bracket and a distal end and a distal link having a proximal end pivotally attached to the distal end of said proximal link and a distal free end for selectively attaching to and detaching from said main bracket, said main bracket having a retention element for selectively locking said distal free end of said distal link thereto, a drive wheel rotatably coupled to said clamp and having a surface exposed for frictional engagement with the shaft of the endoscope, said drive wheel being rotatable about an axis that is perpendicular to the axis defined by the endoscope so that when the surface of said drive wheel engages the shaft of the endoscope rotation of the drive wheel moves the endoscope in the axis defined by the endoscope, a second wheel coupled to said clamp and having a surface exposed for frictional engagement with the shaft of the endoscope, said second wheel being rotatable about an axis that is perpendicular to the axis defined by the endoscope and lies in a common plane with the axis of rotation of said drive wheel, the exposed surface of said second wheel being resiliently mounted with respect to said clamp so that the position of the exposed surface of said second wheel relative to said drive wheel yields in a direction perpendicular to both the axis defined by the endoscope and the axis of rotation of said second wheel to accommodate the outer diameter of the shaft of the endoscope and to apply a pre-load to the shaft with sufficient force to prevent slippage of the endoscope relative to said device, and a motor mechanically coupled to said drive wheel for rotating said drive wheel to cause controlled axial motion of endoscope within the body of the patient.

12. The device of claim 11 further comprising a spring coupled to said second wheel for urging the exposed surface of said second wheel against the shaft of the endoscope to providing a pre-load thereagainst.

13. The device of claim 11 further comprising a controller in communication with said motor for selectively operating said motor.

14. The device of claim 11 wherein said device has exposed outer surfaces that are formed from steam-autoclavable material.

15. The device of claim 11 wherein said drive wheel has a circumferential surface defining a V-shaped groove disposed in a plane perpendicular to the axis of rotation of said drive wheel, said V-shaped groove being sized and constructed to engage the shaft of the endoscope.

* * * * *

UNITED STATES PATENT AND TRADEMARK OFFICE
CERTIFICATE OF CORRECTION

PATENT NO. : 5,540,649                     Page 1 of 2

DATED      : July 30, 1996

INVENTOR(S) : Leonard Bonnell et al.

It is certified that error appears in the above-identified patent and that said Letters Patent is hereby corrected as shown below:

On the cover page, under "References Cited, U.S. Patent Documents" add the following references:

| | | | |
|---|---|---|---|
| 4,229,136 | 10/21/80 | Panissidi | 414/673 |
| 4,652,204 | 03/24/87 | Arnett | 414/751 |
| 4,659,280 | 04/21/87 | Akeel | 414/720 |
| 4,784,010 | 11/15/88 | Wood, et al. | 74/479 |
| 4,863,133 | 09/05/89 | Bonnell | 248/278 |
| 4,881,709 | 11/21/89 | Nakamura | 248/281.1 |
| 5,054,725 | 10/08/91 | Bucefari, et al. | 248/123.1 |
| 5,184,601 | 02/09/93 | Putman | 128/4 |
| 5,205,522 | 04/27/93 | Nakamura | 248/123.1 |
| 5,251,156 | 10/05/93 | Heier, et al. | 364/559 |

On the cover page, under "References Cited, Other Publications" add the following references:

M. Moran, "Stationary and Automated Laparoscopically Assisted Technologies", 1993, *J. Laparoendoscopic Surgery*, Vol. 3, No. 3, pp 221-227.

UNITED STATES PATENT AND TRADEMARK OFFICE
CERTIFICATE OF CORRECTION

PATENT NO. : 5,540,649

DATED : July 30, 1996

INVENTOR(S) : Leonard Bonnell et al.

It is certified that error appears in the above-identified patent and that said Letters Patent is hereby corrected as shown below:

On the cover page, under "References Cited, Other Publications" add the following references:

G. Berci, et al., "New Ideas and Improved Instrumentation for Laparoscopic Cholecystectomy", 1991, Surgical Endoscopy, No. 5, pp. 1-3.

A. Cuschieri, "Minimal Access Surgery and the Future of Interventional Laparoscopy", Mar. 1991, Amer. J. Surgery, Vol. 161, pp. 404-407.

L. K. Nathanson, et al., "Laparoscopic Cholecystectomy: the Dundee Technique", Feb. 1991, Br. J. Surg., Vol. 78, pp 155-159.

Leonard Medical, Inc., "Instrument Control: Manageable and Tireless", Apr., 1993, Leonard Arm U.S. Patent No. 4,863,133.

Signed and Sealed this

Second Day of June, 1998

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO.   : 5,540,649

DATED        : July 30, 1996

INVENTOR(S)  : Leonard Bonnell, John G. Aceti

It is certified that error appears in the above-identified patent and that said Letters Patent is hereby corrected as shown below:

Col. 5, line 38, "motors" should be --motor--.

Signed and Sealed this

Thirteenth Day of October 1998

Attest:

BRUCE LEHMAN

Attesting Officer

Commissioner of Patents and Trademarks